United States Patent
Zhang

(10) Patent No.: US 11,821,759 B1
(45) Date of Patent: Nov. 21, 2023

(54) AUXILIARY DEVICE FOR DETECTING DAMP-HOT PERFORMANCE OF FABRIC

(71) Applicant: SOOCHOW UNIVERSITY, Suzhou (CN)

(72) Inventor: Lili Zhang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 18/020,917

(22) PCT Filed: Sep. 20, 2022

(86) PCT No.: PCT/CN2022/119869
§ 371 (c)(1),
(2) Date: Feb. 10, 2023

(51) Int. Cl.
*G01D 21/02* (2006.01)
*G01N 33/36* (2006.01)

(52) U.S. Cl.
CPC .......... *G01D 21/02* (2013.01); *G01N 33/367* (2013.01)

(58) Field of Classification Search
CPC ..................................................... G01D 21/02
See application file for complete search history.

(56) References Cited

U.S. PATENT DOCUMENTS

| | | | |
|---|---|---|---|
| 6,116,777 A * | 9/2000 | Pause | G01N 33/36 374/43 |
| 7,680,638 B2 * | 3/2010 | Kim | G01N 33/367 374/134 |
| 2007/0151374 A1 * | 7/2007 | Polegato Moretti | G01N 33/367 73/865.6 |

FOREIGN PATENT DOCUMENTS

| | | |
|---|---|---|
| CN | 1844920 A | 10/2006 |
| CN | 201163280 Y | 12/2008 |
| CN | 101551379 A | 10/2009 |
| CN | 102243193 A | 11/2011 |
| CN | 102507628 A | 6/2012 |
| CN | 204556461 U | 8/2015 |
| CN | 207779941 U | 8/2018 |
| CN | 109100496 A | 12/2018 |
| CN | 109632874 A | 4/2019 |
| CN | 209589292 U | 11/2019 |
| CN | 210401113 U | 4/2020 |

(Continued)

OTHER PUBLICATIONS

Gang Xiong et a., "SDJ/W25 Constant Humidity High/Low Temperature Test Chamber" Terminological Interpretion, No. 5, pp. 49-53, ISSN: 1004-7204 (Oct. 31, 2009).

*Primary Examiner* — Kristina M Deherrera
*Assistant Examiner* — Jean F Morello
(74) *Attorney, Agent, or Firm* — SZDC LAW P.C.

(57) ABSTRACT

The present invention provides an auxiliary device for detecting a damp-hot performance of fabric, including: a working table provided with a mounting frame; a first fabric fixing plate fixedly provided on the working table; a second fabric fixing plate fixedly provided on the mounting frame; a rotating part rotatably connected between the first fabric fixing plate and the second fabric fixing plate; a simulation block detachably connected to the rotating part and provided with a simulation layer; and a rotating motor connected to the rotating part; wherein a damp-hot detection cavity is enclosed among the to-be-detected fabric, the first fabric fixing plate and the second fabric fixing plate, and the damp-hot detection cavity is provided with a damp-hot air supply device and a temperature and humidity sensor group. Damp-hot air is introduced into the damp-hot detection cavity, and the simulation block rotates.

9 Claims, 3 Drawing Sheets

(56) References Cited

FOREIGN PATENT DOCUMENTS

| | | |
|---|---|---|
| CN | 211346883 U | 8/2020 |
| CN | 213875368 U | 8/2021 |
| CN | 114755263 A | 7/2022 |
| JP | 2003050541 A | 2/2003 |
| WO | 2021261257 A1 | 12/2021 |

* cited by examiner

US 11,821,759 B1

AUXILIARY DEVICE FOR DETECTING DAMP-HOT PERFORMANCE OF FABRIC

This application is the National Stage Application of PCT/CN2022/119869, filed on Sep. 20, 2022, which claims priority to Chinese Patent Application No. 202210676838.7, filed on Jun. 16, 2022, which is incorporated by reference for all purposes as if fully set forth herein.

FIELD OF THE DISCLOSURE

The present invention relates to the field of fabric damp-hot performance testing technologies, and particularly to an auxiliary device for detecting a damp-hot performance of fabric.

BACKGROUND OF THE DISCLOSURE

Under continuous promotion of research and development technologies, fabric made of various novel materials and mixed materials continuously emerge. Performance requirements of the fabric are different according to different use scenarios. Therefore, performances of the fabric are required to be detected and compared to select the most suitable fabric corresponding to each scenario.

A damp-hot performance of the fabric is one of important indexes for measuring features of the fabric. However, in a prior art, when the damp-hot performance of the fabric is detected, a human body surface environment or the use scenario where the fabric is located cannot be well simulated, such that a detection result of the damp-hot performance of the fabric cannot be well consistent with the damp-hot performance of the fabric in an actual use environment, resulting in low accuracy of the detection result and even an invalid detection result.

SUMMARY OF THE DISCLOSURE

The present invention provides an auxiliary device for detecting a damp-hot performance of fabric, so as to allow a detection result to be consistent with an actual use environment of the fabric, thereby improving accuracy of the detection result, and ensuring that the detection result is valid.

An auxiliary device for detecting a damp-hot performance of fabric, comprising:

a working table provided with a mounting frame;

a first fabric fixing plate fixedly provided on the mounting frame and configured to detachably fix the to-be-detected fabric;

a second fabric fixing plate fixedly provided on the working table and configured to detachably fix the to-be-detected fabric;

a rotating part vertically and rotatably connected between the first fabric fixing plate and the second fabric fixing plate which are oppositely arranged up and down;

a simulation block detachably connected to the rotating part, a simulation layer for simulating a use environment of the fabric being provided on a side surface of the simulation block apart from the rotating part; and a rotating motor connected to the rotating part to drive the rotating part to rotate;

wherein after the to-be-detected fabric is fixed by the first fabric fixing plate and the second fabric fixing plate, a damp-hot detection cavity is enclosed among the to-be-detected fabric, the first fabric fixing plate and the second fabric fixing plate, and the damp-hot detection cavity is provided with a damp-hot air supply device for providing damp-hot air and a temperature and humidity sensor group for detecting a temperature and humidity;

the simulation block is provided with a cavity, the cavity is distributed along the simulation layer, the rotating part is provided with a first channel, the damp-hot air supply device is communicated with the first channel through a first pipe, the first pipe is rotatably connected with the rotating part, the simulation block is provided with a second channel communicated with the cavity, and after the simulation block is detachably connected with the rotating part, the second channel is communicated with the first channel.

In summary, the present invention has at least the following beneficial effects: in the present invention, the to-be-detected fabric is fixed by the first fabric fixing plate and the second fabric fixing plate, the fixed to-be-detected fabric, the first fabric fixing plate and the second fabric fixing plate jointly enclose the damp-hot detection cavity, the damp-hot air is introduced into the damp-hot detection cavity by the damp-hot air supply device, the rotating part is driven to rotate by the rotating motor, and the rotating part drives the simulation block with the simulation layer for simulating the use environment of the fabric to rotate, thereby accurately simulating the damp-hot performance of the to-be-detected fabric in the use environment, then improving the accuracy of the detection result, and ensuring that the detection result is accurate and valid; temperature and humidity detection is then performed by the temperature and humidity sensor group, thus providing accurate reference data for the detection result.

Figure 1:
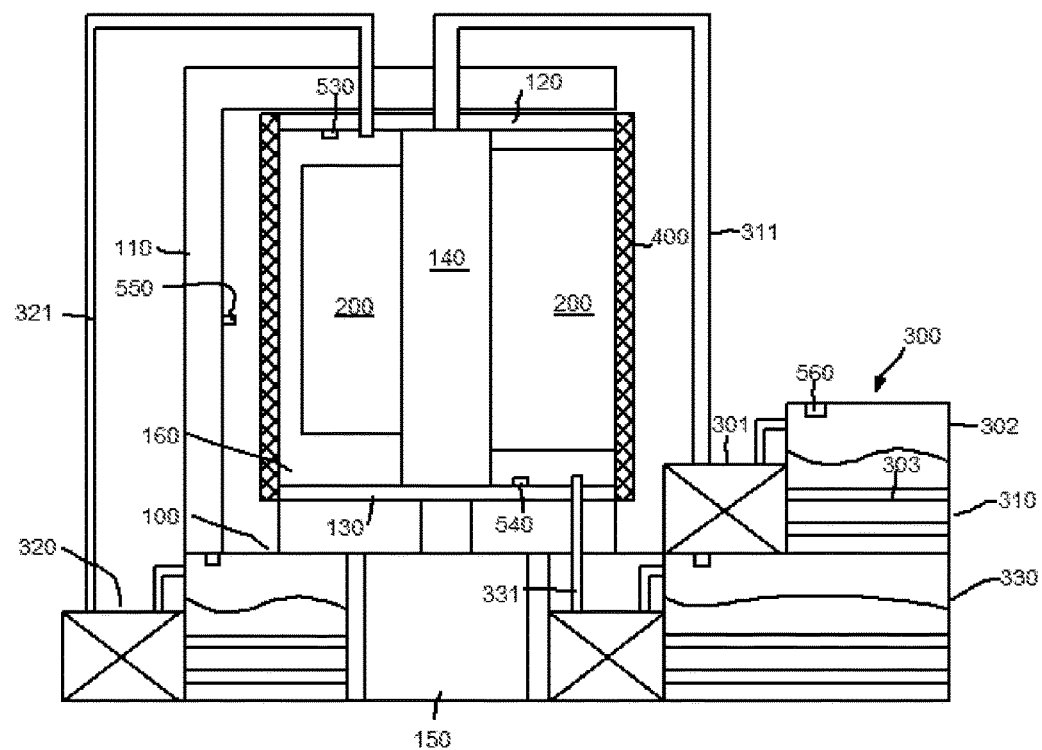
FIG. 1 is a schematic structural diagram of an auxiliary device for detecting a damp-hot performance of fabric according to some embodiments of the present invention.

Reference numerals:

100. working table; 110. mounting frame; 120. first fabric fixing plate; 130. second fabric fixing plate; 140. rotating part; 141. first channel; 142. first clamping groove; 143. second clamping groove; 144. third clamping groove; 150. rotating motor; 160. damp-hot detection cavity; 170. magnet; 180. hoop;

200. simulation block; 210. simulation layer; 220. cavity; 230. second channel; 240. spring cavity; 241. spring; 250. concave block; 260. clamping block;

300. damp-hot air supply device; 310. first supply device; 311. first pipe; 320. second supply device; 321. second pipe; 330. third supply device; 331. third pipe; 301. fan; 302. water tank; 303. electric heating tube;

400. to-be-detected fabric;

510. first temperature and humidity sensor; 520. second temperature and humidity sensor; 530. third temperature and humidity sensor; 540. fourth temperature and humidity sensor; 550. fifth temperature and humidity sensor; 560. sixth temperature and humidity sensor.

DETAILED DESCRIPTION OF PREFERRED EMBODIMENTS

Embodiments of the present invention will be described in detail below with reference to the accompanying drawings.

As shown in FIG. 1, the present embodiment provides an auxiliary device for detecting a damp-hot performance of fabric, including:

a working table 100 provided with a mounting frame 110;

a first fabric fixing plate 120 fixedly provided on the working table 100 and configured to detachably fix the to-be-detected fabric 400;

a second fabric fixing plate 130 fixedly provided on the mounting frame 110 and configured to detachably fix the to-be-detected fabric 400; a rotating part 140 vertically and rotatably connected between the first fabric fixing plate 120 and the second fabric fixing plate 130 which are oppositely arranged up and down;

a simulation block 200 detachably connected to the rotating part 140, a simulation layer 210 for simulating a use environment of the fabric being provided on a side surface of the simulation block apart from the rotating part 140; and a rotating motor 150 connected to the rotating part 140 to drive the rotating part 140 to rotate;

wherein after the to-be-detected fabric 400 is fixed by the first fabric fixing plate 120 and the second fabric fixing plate 130, a damp-hot detection cavity 160 is enclosed among the to-be-detected fabric 400, the first fabric fixing plate 120 and the second fabric fixing plate 130, and the damp-hot detection cavity 160 is provided with a damp-hot air supply device 300 for providing damp-hot air and a temperature and humidity sensor group for detecting a temperature and humidity.

In the present embodiment, the auxiliary device for detecting a damp-hot performance of fabric plays an auxiliary role for simulating the use environment of the to-be-detected fabric 400 and providing temperature and humidity reference data (collected by the temperature and humidity sensor group) for improving accuracy of a detection result, and it can be understood that a device directly configured to detect the damp-hot performance of the fabric can be s fabric thermal resistance and damp resistance tester or another existing detection device, which is not repeated in the present embodiment. In an actual detection environment, the auxiliary device for detecting a damp-hot performance of fabric according to the embodiment of the present application and the fabric thermal resistance and damp resistance tester are used in cooperation, so as to jointly detect the damp-hot performance of the fabric.

It should be noted that the simulation layer 210 for simulating the use environment of the fabric can be detachably assembled and disassembled along with the simulation block 200, and when different use environments are simulated, material selection can be performed according to the use environment of the to-be-detected fabric 400, and if the to-be-detected fabric 400 is used for a human body, a material of the simulation layer 210 can be selected from materials similar to smart foam of robot skin, or the like.

In other simulation environments, the to-be-detected fabric 400 may also be used in a wooden environment, and the material of the simulation layer 210 may be a corresponding wooden material; for another example, if the to-be-detected fabric 400 is used in a metal environment, the material of the simulation layer 210 may be a corresponding metal material; for other plastic environments, or the like, the material of the simulation layer 210 may be a corresponding material; the simulation layer 210 made of the corresponding material is manufactured in advance according to the use environment of the to-be-detected fabric 400.

Before detection, the to-be-detected fabric 400 is fixed by the first fabric fixing plate 120 and the second fabric fixing plate 130, cross sections of the first fabric fixing plate 120 and the second fabric fixing plate 130 are approximately round, the damp-hot detection cavity 160 enclosed among the to-be-detected fabric 400, the first fabric fixing plate 120 and the second fabric fixing plate 130 is similar to a barrel-shaped structure, the damp-hot air is introduced into the damp-hot detection cavity 160 by the damp-hot air supply device 300, and meanwhile, the rotating motor 150 is started, the rotating motor 150 drives the rotating part 140 to rotate, and the rotating part 140 drives the simulation layer 210 and the simulation block 200 to rotate, thereby accurately simulating the damp-hot performance of the to-be-detected fabric 400 in the use environment, then improving accuracy of the detection result, and ensuring that the detection result is accurate and valid; temperature and humidity detection is then performed by the temperature and humidity sensor group, thus providing accurate reference data for the detection result.

A shape and size of the simulation block 200 can be changed, and in a specific use environment, simulation blocks 200 of different models can be configured according to a use occasion of the fabric. When the rotating part 140 rotates, the simulation block 200 performs a rotation operation in the damp-hot detection cavity 160 along with the rotating part 140, such that a situation where the fabric is in direct contact with the human body and friction exists can be simulated in some cases, a situation where the fabric is not in contact with the human body can be simulated in other cases, and therefore, the auxiliary device for detecting a damp-hot performance has wider applicability.

Figure 4:
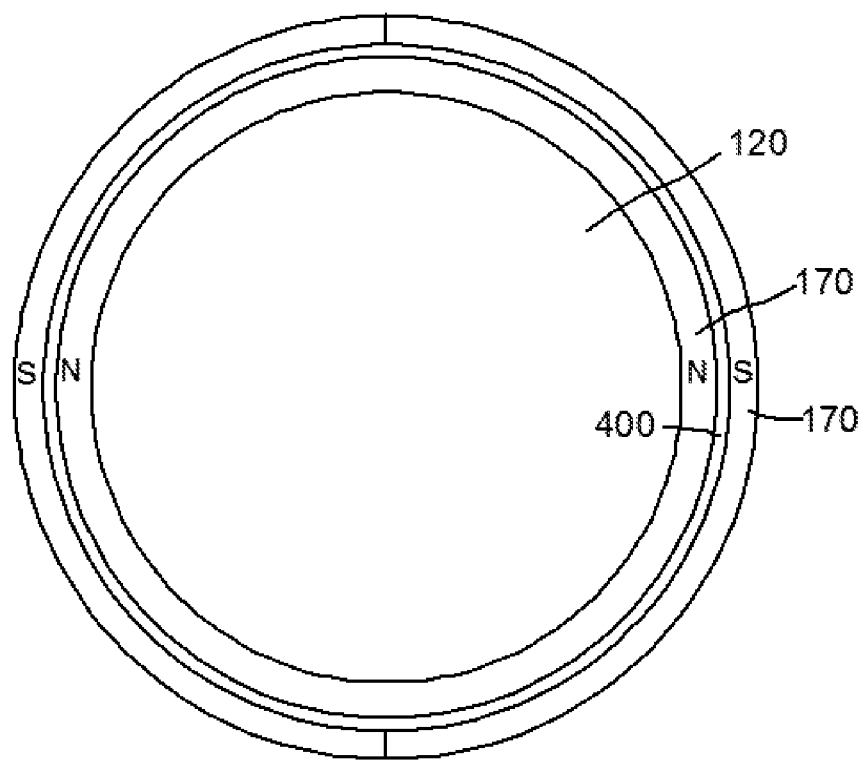
FIG. 4 is a schematic structural diagram in which to-be-detected fabric is fixed by a magnet in some embodiments of the present invention.
Figure 5:
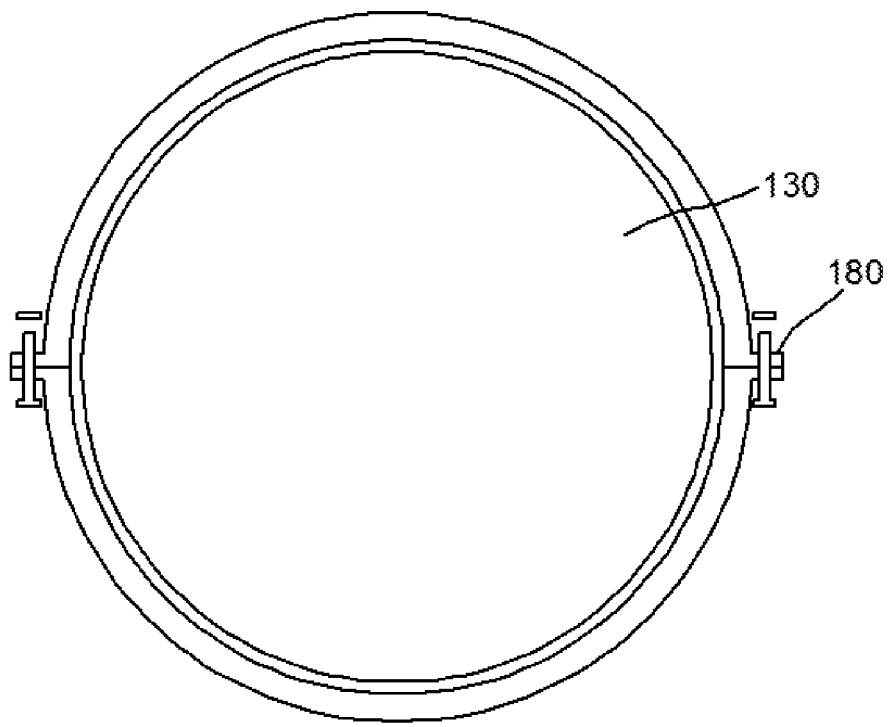
FIG. 5 is a schematic structural diagram in which the to-be-detected fabric is fixed by a hoop in some embodiments of the present invention.

In order to fix the to-be-detected fabric 400 conveniently, in some embodiments, as shown in FIGS. 4 and 5, the first fabric fixing plate 120 and the second fabric fixing plate 130 are detachably connected with the to-be-detected fabric 400 by hook and loop fasteners or magnets 170 or hoops 180. In this solution, the hook and loop fasteners or magnets 170 or hoops 180 or other existing detachable connection methods are adopted; for example, a magnet 170 with N polarity and a magnet 170 with S polarity are provided on the first fabric fixing plate 120 and the second fabric fixing plate 130 respectively, and the to-be-detected fabric 400 is clamped between the 2 magnets 170 with opposite polarity, so as to realize fixation; for another example, when the first fabric fixing plate 120 and the second fabric fixing plate 130 are circular plates, by the hoops 180 and corresponding bolts and nuts, one end of the to-be-detected fabric 400 is clamped between one hoop and the first fabric fixing plate 120, and the other end thereof is clamped between the other hoop 180 and the second fabric fixing plate 130, so as to realize fixation.

By adopting the above fixing mode, the to-be-detected fabric 400 can be conveniently detached from the first fabric fixing plate 120 and the second fabric fixing plate 130, and since the damp-hot detection cavity 160 enclosed by the to-be-detected fabric 400, the first fabric fixing plate 120 and the second fabric fixing plate 130 is an annular cavity, the use environment of the to-be-detected fabric 400 can be well simulated without absolute sealing, only with relative sealing and even without sealing.

Figure 3:
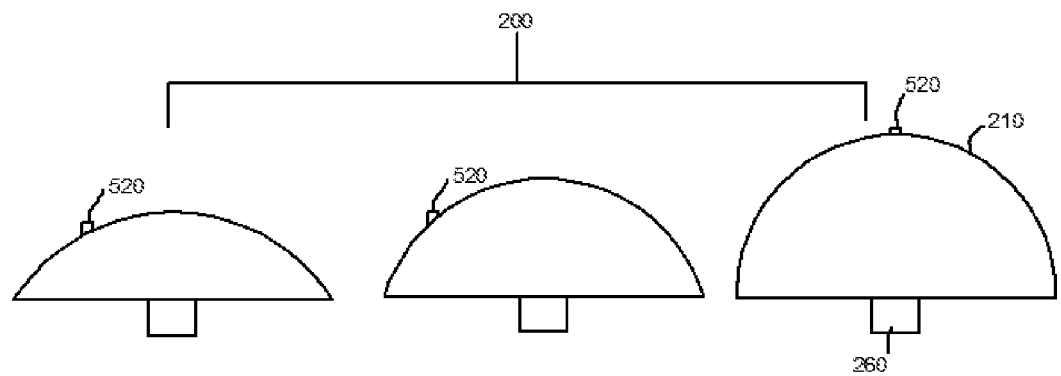
FIG. 3 is a schematic structural diagram of simulation blocks with different sizes in some embodiments of the present invention.

In order to accurately simulate the use environment of the to-be-detected fabric 400, in some embodiments, as shown in FIG. 3, there are a plurality of simulation blocks 200 with different sizes, such that there is a gap between the simulation block 200 and the to-be-detected fabric 400, or the simulation block 200 and the to-be-detected fabric 400 are in contact with each other, or the simulation block 200 abut against the to-be-detected fabric 400. In this solution, the simulation blocks 200 with different sizes can simulate real conditions where the to-be-detected fabric 400 is not in contact with the use environment, is in contact with the use environment and is pressed against the use environment, such that the accuracy of the detection result is further improved; in practical applications, the simulation block 200 may include a semi-cylinder or a sector-shaped cylinder and a clamping block 260, the clamping block 260 is detachably connected with the rotating part 140, the semi-cylinder or the sector-shaped cylinder is fixedly connected with the clamping block 260, and the actual conditions where the to-be-detected fabric 400 is not in contact with the use environment, is in contact with the use environment and is pressed against the use environment can be changed by the semi-cylinders with different radii or the sector-shaped cylinders with different radians; in some embodiments, the plural simulation blocks 200 with different sizes may be used simultaneously; in other embodiments, the plural simulation blocks 200 with different sizes may be used alternatively. In some embodiments, the rotating part 140 may be a cylinder, a rectangular cylinder, or a polygonal cylinder with five or more sides.

Figure 2:
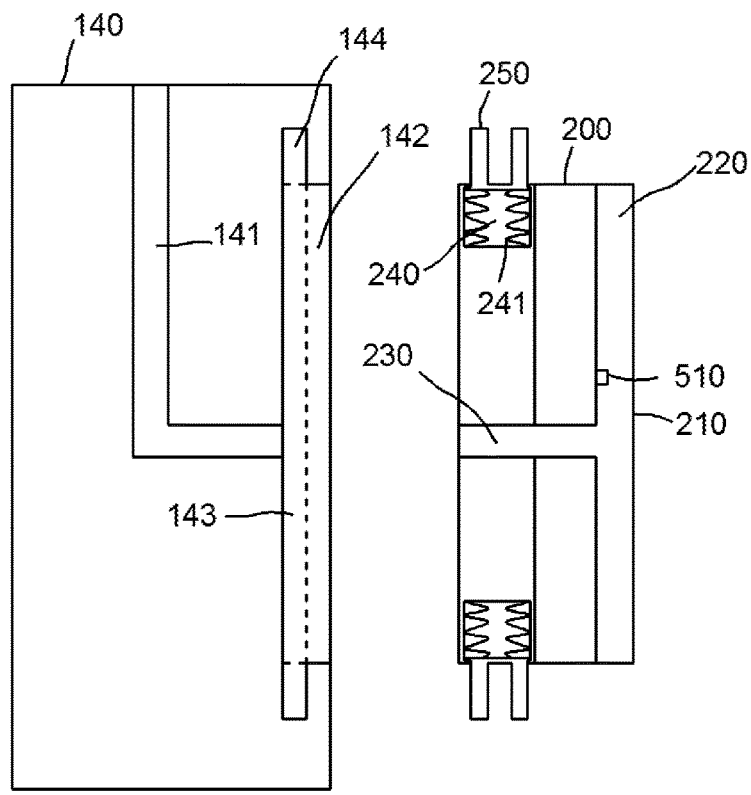
FIG. 2 is a schematic structural diagram of a first channel, a second channel and a cavity in some embodiments of the present invention.

In order to further accurately simulate the use environment of the to-be-detected fabric 400, in some embodiments, as shown in FIG. 2, the simulation block 200 is provided with a cavity 220, the cavity 220 is distributed along the simulation layer 210, the rotating part 140 is provided with a first channel 141, the damp-hot air supply device 300 is communicated with the first channel 141 through a first pipe 311, the first pipe 311 is rotatably connected with the rotating part 140, the simulation block 200 is provided with a second channel 230 communicated with the cavity 220, and after the simulation block 200 is connected with the rotating part 140, the second channel 230 is communicated with the first channel 141. In this solution, the damp-hot air is introduced into the cavity 220 by the damp-hot air supply device 300, thereby accurately simulating the damp-hot air emitted from inside to outside by an object in the use environment of the to-be-detected fabric 400, then accurately simulating the use environment of the to-be-detected fabric 400, improving the accuracy of the detection result, and particularly accurately simulating the environment when the to-be-detected fabric 400 is used for the human body.

Referring to FIG. 2, in some embodiments, each of a top and a bottom of the simulation block 200 is provided with a spring cavity 240, a spring 241 is provided in the spring cavity 240, a concave block 250 is slidably connected to the spring cavity 240, the concave block 250 is telescopically slid inside and outside the spring cavity 240 through the spring 241, an outer side surface of the rotating part 140 is sequentially provided with a first clamping groove 142 and a second clamping groove 143 which are communicated from outside to inside, and a size of the second clamping groove 143 in a length direction is greater than a size of the first clamping groove 142 in the length direction, such that the second clamping groove 143 exceeds the first clamping groove 142 to form a third clamping groove 144; the third clamping groove 144 is a part of the second clamping groove 143, 2 third clamping grooves 144 may be provided and located at an upper side and a lower side respectively, and 2 clamping walls correspond to the 2 concave blocks 250 in a normal state one by one; the third clamping groove 144 is matched with a protrusion at one side of the concave block 250, and when the concave block 250 retracts into the spring cavity 240 through the spring 241, the clamping block 260 of the simulation block 200 is partially inserted into the first clamping groove 142 and the second clamping groove 143 in sequence, and under the action of the spring 241, the concave block 250 is embedded into the third clamping groove 144, such that the simulation block 200 is detachably connected with the rotating part 140; during disassembly, an exposed part of the concave block 250 is pressed, such that the concave block 250 can be separated from the third clamping groove 144, and the simulation block 200 can be pulled out.

In order to improve reliability of the temperature and humidity reference data, in some embodiments, the temperature and humidity sensor group includes a first temperature and humidity sensor 510, a second temperature and humidity sensor 520, a third temperature and humidity sensor 530, a fourth temperature and humidity sensor 540, and a fifth temperature and humidity sensor 550, which are electrically connected to the damp-hot air supply device 300 and can control corresponding damp-hot air supply amounts of the damp-hot air supply device 300 and other damp-hot air related parameters, for example, but not limited to, a temperature and humidity.

The first temperature and humidity sensor 510 is provided in the cavity 220, the second temperature and humidity sensor 520 is provided on an outer side surface of the simulation layer 210, the third temperature and humidity sensor 530 is provided on a side surface of the first fabric fixing plate 120 facing the second fabric fixing plate 130, the fourth temperature and humidity sensor 540 is provided on a side surface of the second fabric fixing plate 130 facing the first fabric fixing plate 120, and the fifth temperature and humidity sensor 550 is provided on a side of the mounting frame 110 close to the to-be-detected fabric 400. In this solution, the reliability of the temperature and humidity reference data can be improved by the temperature and humidity reference data collected by each of the first temperature and humidity sensor 510, the second temperature and humidity sensor 520, the third temperature and humidity sensor 530, the fourth temperature and humidity sensor 540 and the fifth temperature and humidity sensor 550, the accuracy of the detection result can be accurately checked, and meanwhile, reliability evidence can be provided for the accuracy of the detection result, and authenticity of the detection result can be proved indirectly. The second temperature and humidity sensor 520 may be located on an end surface of the outer side surface of the simulation layer 210 closest to the to-be-detected fabric 400, and when the simulation block 200 rotates and the to-be-detected fabric 400 is in contact with or is pressed against the simulation layer 210, the second temperature and humidity sensor 520 may be in direct contact with the to-be-detected fabric 400, and data collected by the second temperature and humidity sensor 520 may be affected by the temperature and humidity of the to-be-detected fabric 400; that is, the second temperature and humidity sensor 520 may provide accurate and reliable temperature and humidity reference data for the detection result, and the reference data may even be used as one kind of detection data of the detection result, thereby effectively improving the accuracy of the detection result; certainly, in other embodiments, the second temperature and humidity sensor 520 may be located on an end surface of the outer side surface of the simulation layer 210 not close to the to-be-detected fabric 400, and when the simulation block 200 rotates, the second temperature and humidity sensor 520 is not in contact with the to-be-detected fabric 400, and the data collected by the second temperature and humidity sensor 520 is temperature and humidity data of the outer side surface of the simulation layer 210.

In order to facilitate control over the simulated use environment of the to-be-detected fabric 400, in some embodiments, the damp-hot air supply device 300 includes a first supply device 310, a second supply device 320, and a third supply device 330, the first supply device 310 is communicated with the first channel 141 through the first pipe 311, the second supply device 320 is communicated with a top side of the damp-hot detection cavity 160 through a second pipe 321, and the third supply device 330 is communicated with a bottom side of the damp-hot detection cavity 160 through a third pipe 331. In this solution, by the first supply device 310, the second supply device 320 and the third supply device 330, the damp-hot air with different temperatures and humidity can be introduced to control the simulated use environment of the to-be-detected fabric 400, thereby accurately simulating the use environment of the to-be-detected fabric 400.

In some embodiments, each of the first supply device 310, the second supply device 320, and the third supply device 330 includes a fan 301, a water tank 302, and an electric heating tube 303, the electric heating tube 303 is provided in the water tank 302, the first pipe 311, the second pipe 321, and the third pipe 331 are connected with the corresponding fans 301 respectively, and the fan 301 is connected to an inner upper side of the water tank 302 through a fourth pipe to extract the damp-hot air.

In some embodiments, a sixth temperature and humidity sensor 560 is provided on an inner top side of the water tank 302. In this solution, the temperature and humidity of the damp-hot air inside the water tank 302 are detected by the sixth temperature and humidity sensor 560, and the work of the electric heating tube 303 can be accurately controlled.

In some embodiments, each of the first temperature and humidity sensor 510, the third temperature and humidity sensor 530, the fourth temperature and humidity sensor 540, and the sixth temperature and humidity sensor 560 includes a temperature sensor and a humidity sensor, and the temperature sensor is provided with a temperature control circuit.

Figure 6:
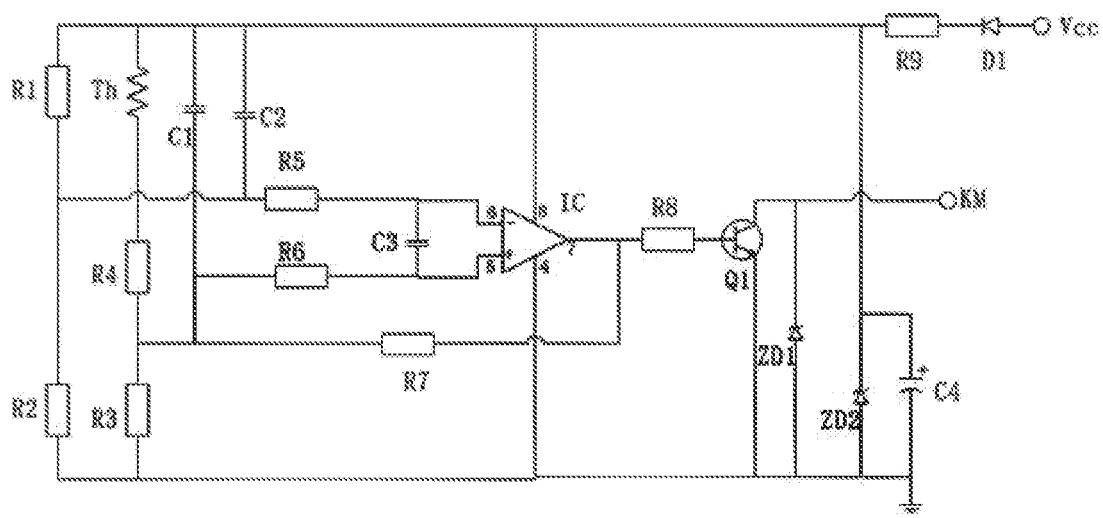
FIG. 6 is a schematic circuit diagram of a temperature control circuit in some embodiments of the present invention.

In some embodiments, as shown in FIG. 6, the temperature control circuit includes a resistor R1, a resistor R2, a resistor R3, a resistor R4, a resistor R5, a resistor R6, a resistor R7, a resistor R8, a resistor R9, a capacitor C1, a capacitor C2, a capacitor C3, a capacitor C4, a diode D1, a voltage regulator tube ZD1, a voltage regulator tube ZD2, a triode Q1, an operational amplifier chip IC, a thermistor RT and a relay KM;

an anode of the diode D1 is externally connected with a power end Vcc, a cathode of the diode D1 is connected with one end of the resistor R9, the other end of the resistor R9 is connected with one end of the resistor R1, one end of the thermistor RT, one end of the capacitor C1, one end of the capacitor C2, a pin 8 of the operational amplifier chip IC, a cathode of the voltage regulator tube ZD2 and an anode of the capacitor C4, the other end of the resistor R1 is connected with one end of the resistor R2, the other end of the capacitor C2 and one end of the resistor R5, the other end of the thermistor RT is connected with one end of the resistor R4, the other end of the capacitor C1 is connected with one end of the resistor R6, the other end of the resistor R4, one end of the resistor R3 and one end of the resistor R7, the other end of the resistor R5 is connected with one end of the capacitor C3 and a pin 6 of the operational amplifier chip IC, the other end of the resistor R6 is connected with the other end of the capacitor C3 and a pin 5 of the operational amplifier chip IC 8, the other end of the resistor R7 is connected with a pin 7 of the operational amplifier chip IC and one end of the resistor R8, the other end of the resistor R8 is connected with a base of the triode Q1, a collector of the triode Q1 is connected with the relay KM and a cathode of the voltage regulator tube ZD1, and one end of the resistor R2, one end of the resistor R3, a pin 4 of the operational amplifier chip IC, an emitter of the triode Q1, an anode of the voltage regulator tube ZD2, an anode of the voltage regulator tube ZD1 and a cathode of the capacitor C4 are all grounded;

the thermistor RT is representation of the temperature sensor in the circuit, and the relay KM is connected with the electric heating tube 303 to control the work of the electric heating tube 303; in practice, a switch contact of the relay KM is connected in series in a working circuit of the electric heating tube 303 to control the working circuit of the electric heating tube 303 to be turned on and off, that is, to control the work of the electric heating tube 303;

the operational amplifier chip IC is LM2904, the pin 6 thereof is an inverting end, and the pin 5 thereof is a non-inverting end; the power end Vcc may be 12VDC, a voltage between the resistor R1 and the resistor R2 is a reference voltage, and a voltage between the resistor R4 and the resistor R3 is a comparison voltage; when the reference voltage is greater than the comparison voltage, the pin 7 of the operational amplifier chip IC is at a low level; when the reference voltage is less than the comparison voltage, the pin 7 of the operational amplifier chip IC is at a high level;

the temperature sensor is a negative temperature coefficient thermistor or a positive temperature coefficient thermistor;

when the temperature sensor is a negative temperature coefficient thermistor, the electric heating tube 303 is connected with a normally closed contact of the relay KM; when an environmental temperature detected by the temperature sensor rises, a resistance value of the thermistor RT becomes smaller, and when the resistance value changes to a certain value, the comparison voltage is greater than the reference voltage, the pin 7 of the operational amplifier chip IC is at a high level, the triode Q1 is switched on, a coil of the relay KM is electrified, the normally closed contact of the relay KM is disconnected, and the electric heating tube 303 stops working; when the environmental temperature detected by the temperature sensor is reduced, the resistance value of the thermistor RT is increased, and when the resistance value is changed to a certain value, the comparison voltage is less than the reference voltage, the pin 7 of the operational amplifier chip IC is at a low level, the triode Q1 is switched off, the coil of the relay KM is powered off, the normally closed contact of the relay KM is closed, and the electric heating tube 303 works;

when the temperature sensor is a positive temperature coefficient thermistor, the electric heating tube 303 is connected with a normally open contact of the relay KM; when the environmental temperature detected by the temperature sensor rises, the resistance value of the thermistor RT becomes greater, and when the resistance value changes to a certain value, the comparison voltage is less than the reference voltage, the pin 7 of the operational amplifier chip IC is at a low level, the triode Q1 is switched off, the coil of the relay KM is powered off, the normally open contact of the relay KM is disconnected, and the electric heating tube 303 stops working; when the environmental temperature detected by the temperature sensor is reduced, the resistance value of the thermistor RT is decreased, and when the resistance value is changed to a certain value, the comparison voltage is greater than the reference voltage, the pin 7 of the operational amplifier chip IC is at a high level, the triode Q1 is switched on, the coil of the relay KM is electrified, the normally open contact of the relay KM is closed, and the electric heating tube 303 works;

in practical applications, parameters of each electronic component can be properly set through multiple tests; for example, when the to-be-detected fabric 400 is applied to the human body, a skin temperature of the human body is generally 36.1-37° C., and 37° C. is taken as an example; when the temperature is lower than 37° C., the electric heating tube 303 works; when the temperature is higher than 37° C., the electric heating tube 303 stops working; therefore, the temperature of the outer side surface of the simulation layer 210 detected by the temperature sensor is kept at about 37° C., and certainly, an error of +/−1-2° C. can be allowed, which facilitates a reduction of test times and setting of the parameters of each electronic component; for the use environment of other to-be-detected fabric 400 or the environmental temperature detected by the temperature sensor, corresponding parameter setting is performed according to the above description, such that the temperature can be controlled within the corresponding required range, thereby precisely simulating the use environment of the to-be-detected fabric 400, and then improving the accuracy of the detection result.

To sum up, since the respective detection environments are different, parameter setting of the respective temperature control circuits of the first temperature and humidity sensor 510, the third temperature and humidity sensor 530, the fourth temperature and humidity sensor 540, and the sixth temperature and humidity sensor 560 may be different; the first temperature and humidity sensor 510 and/or the sixth temperature and humidity sensor 560, the first supply device 310 and the corresponding temperature control circuit form a first temperature control mechanism, the third temperature and humidity sensor 530 and/or the sixth temperature and humidity sensor 560, the second supply device 320 and the corresponding temperature control circuit form a second temperature control mechanism, the fourth temperature and humidity sensor 540 and/or the sixth temperature and humidity sensor 560, the third supply device 330 and the corresponding temperature control circuit form a third temperature control mechanism, and the first temperature control mechanism, the second temperature control mechanism and the third temperature control mechanism are matched with each other, such that the use environment of the to-be-detected fabric 400 can be precisely simulated, and the accuracy of the detection result is then improved; when two thermistors RT are used, the two thermistors RT may be connected in series into the circuit.

Although the foregoing embodiments have described a number of specific embodiments of the present invention, it will be appreciated by those skilled in the art that various changes or modifications may be made to these embodiments without departing from the principles and spirit of the present invention, and such changes and modifications are intended to fall within the scope of the present invention.

What is claimed is:

1. An auxiliary device for detecting a damp-hot performance of fabric, comprising:
    a working table provided with a mounting frame;
    a first fabric fixing plate fixedly provided on the mounting frame and configured to detachably fix the to-be-detected fabric;
    a second fabric fixing plate fixedly provided on the working table and configured to detachably fix the to-be-detected fabric;
    a rotating part vertically and rotatably connected between the first fabric fixing plate and the second fabric fixing plate which are oppositely arranged up and down;
    a simulation block detachably connected to the rotating part, a simulation layer for simulating a use environment of the fabric being provided on a side surface of the simulation block apart from the rotating part; and
    a rotating motor connected to the rotating part to drive the rotating part to rotate;
    wherein after the to-be-detected fabric is fixed by the first fabric fixing plate and the second fabric fixing plate, a damp-hot detection cavity is enclosed among the to-be-detected fabric, the first fabric fixing plate and the second fabric fixing plate, and the damp-hot detection cavity is provided with a damp-hot air supply device for providing damp-hot air and a temperature and humidity sensor group for detecting a temperature and humidity;
    the simulation block is provided with a cavity, the cavity is distributed along the simulation layer, the rotating part is provided with a first channel, the damp-hot air supply device is communicated with the first channel through a first pipe, the first pipe is rotatably connected with the rotating part, the simulation block is provided with a second channel communicated with the cavity, and after the simulation block is detachably connected with the rotating part, the second channel is communicated with the first channel.

2. The auxiliary device for detecting a damp-hot performance of fabric according to claim 1, wherein there are a plurality of simulation blocks with different sizes, such that there is a gap between the simulation block and the to-be-detected fabric, or the simulation block and the to-be-detected fabric are in contact with each other.

3. The auxiliary device for detecting a damp-hot performance of fabric according to claim 1, wherein the temperature and humidity sensor group comprises a first temperature and humidity sensor, a second temperature and humidity sensor, a third temperature and humidity sensor, a fourth temperature and humidity sensor, and a fifth temperature and humidity sensor; the first temperature and humidity sensor is provided in the cavity, the second temperature and humidity sensor is provided on an outer side surface of the simulation layer, the third temperature and humidity sensor is provided on a side surface of the first fabric fixing plate facing the second fabric fixing plate, the fourth temperature and humidity sensor is provided on a side surface of the second fabric fixing plate facing the first fabric fixing plate, and the fifth temperature and humidity sensor is provided on a side of the mounting frame close to the to-be-detected fabric.

4. The auxiliary device for detecting a damp-hot performance of fabric according to claim 3, wherein the damp-hot air supply device comprises a first supply device, a second supply device, and a third supply device, the first supply device is communicated with the first channel through the first pipe, the second supply device is communicated with a top side of the damp-hot detection cavity through a second pipe, and the third supply device is communicated with a bottom side of the damp-hot detection cavity through a third pipe.

5. The auxiliary device for detecting a damp-hot performance of fabric according to claim 4, wherein each of the first supply device, the second supply device, and the third supply device comprises a fan, a water tank, and an electric heating tube, the electric heating tube is provided in the water tank, the first pipe, the second pipe, and the third pipe are connected with the corresponding fans respectively, and the fan is connected to an inner upper side of the water tank through a fourth pipe to extract the damp-hot air.

6. The auxiliary device for detecting a damp-hot performance of fabric according to claim 5, wherein a sixth temperature and humidity sensor is provided on an inner top side of the water tank.

7. The auxiliary device for detecting a damp-hot performance of fabric according to claim 6, wherein each of the first temperature and humidity sensor, the third temperature and humidity sensor, the fourth temperature and humidity sensor, and the sixth temperature and humidity sensor comprises a temperature sensor and a humidity sensor, and the temperature sensor is provided with a temperature control circuit.

8. The auxiliary device for detecting a damp-hot performance of fabric according to claim 7, wherein the temperature control circuit comprises a resistor R1, a resistor R2, a resistor R3, a resistor R4, a resistor R5, a resistor R6, a resistor R7, a resistor R8, a resistor R9, a capacitor C1, a capacitor C2, a capacitor C3, a capacitor C4, a diode D1, a voltage regulator tube ZD1, a voltage regulator tube ZD2, a triode Q1, an operational amplifier chip IC, a thermistor RT and a relay KM;

an anode of the diode D1 is externally connected with a power end Vcc, a cathode of the diode D1 is connected with one end of the resistor R9, the other end of the resistor R9 is connected with one end of the resistor R1, one end of the thermistor RT, one end of the capacitor C1, one end of the capacitor C2, a pin 8 of the operational amplifier chip IC, a cathode of the voltage regulator tube ZD2 and an anode of the capacitor C4, the other end of the resistor R1 is connected with one end of the resistor R2, the other end of the capacitor C2 and one end of the resistor R5, the other end of the thermistor RT is connected with one end of the resistor R4, the other end of the capacitor C1 is connected with one end of the resistor R6, the other end of the resistor R4, one end of the resistor R3 and one end of the resistor R7, the other end of the resistor R5 is connected with one end of the capacitor C3 and a pin 6 of the operational amplifier chip IC, the other end of the resistor R6 is connected with the other end of the capacitor C3 and a pin 5 of the operational amplifier chip IC 8, the other end of the resistor R7 is connected with a pin 7 of the operational amplifier chip IC and one end of the resistor R8, the other end of the resistor R8 is connected with a base of the triode Q1, a collector of the triode Q1 is connected with the relay KM and a cathode of the voltage regulator tube ZD1, and one end of the resistor R2, one end of the resistor R3, a pin 4 of the operational amplifier chip IC, an emitter of the triode Q1, an anode of the voltage regulator tube ZD2, an anode of the voltage regulator tube ZD1 and a cathode of the capacitor C4 are all grounded;

the thermistor RT is representation of the temperature sensor in the circuit, and the relay KM is connected with the electric heating tube to control the work of the electric heating tube.

9. The auxiliary device for detecting a damp-hot performance of fabric according to claim 1, wherein the first fabric fixing plate and the second fabric fixing plate are detachably connected with the to-be-detected fabric by hook and loop fasteners or magnets or hoops or buttons.

* * * * *